(12) United States Patent
Marchand

(10) Patent No.: US 10,060,561 B2
(45) Date of Patent: Aug. 28, 2018

(54) CONNECTING SYSTEM AND METHOD FOR CONNECTING FLUID-CONDUCTING COMPONENTS

(71) Applicant: Labomatic Instruments AG, Allschwil (CH)

(72) Inventor: Claude Marchand, Hölstein (CH)

(73) Assignee: Labomatic Instruments AG, Allschwil (CH)

(*) Notice: Subject to any disclaimer, the term of this patent is extended or adjusted under 35 U.S.C. 154(b) by 259 days.

(21) Appl. No.: 14/889,725

(22) PCT Filed: May 7, 2014

(86) PCT No.: PCT/EP2014/059345
§ 371 (c)(1),
(2) Date: Mar. 9, 2016

(87) PCT Pub. No.: WO2014/180909
PCT Pub. Date: Nov. 13, 2014

(65) Prior Publication Data
US 2016/0186904 A1    Jun. 30, 2016

(30) Foreign Application Priority Data

May 8, 2013   (DE) .................. 10 2013 208 548

(51) Int. Cl.
*F16L 33/00*       (2006.01)
*F16L 21/08*       (2006.01)
(Continued)

(52) U.S. Cl.
CPC ............. *F16L 21/08* (2013.01); *A61M 39/10* (2013.01); *A61M 39/12* (2013.01); *F16L 13/10* (2013.01); *F16L 37/0985* (2013.01)

(58) Field of Classification Search
CPC ....... F16L 21/08; F16L 33/035; F16L 33/222; F16L 33/225; F16L 33/32; F16L 37/088; F16L 37/091; F16L 37/098
(Continued)

(56) References Cited

U.S. PATENT DOCUMENTS 1,043,683 A * 11/1912 Fieser ................. F16L 33/2076
                                              285/148.16
3,542,405 A * 11/1970 Nalodka ................... F16L 5/10
                                              285/136.1
(Continued)

FOREIGN PATENT DOCUMENTS

DE         4331848 A1      7/1994
DE        20320665 U1     11/2004
(Continued)

*Primary Examiner* — Aaron M Dunwoody
(74) *Attorney, Agent, or Firm* — Mintz Levin Cohn Ferris Glovsky and Popeo, P.C.; Peter F. Corless; Steven M. Jensen

(57) ABSTRACT

A connecting system connects two fluid-conducting components, such as first and second tubes, or a tube and a connecting part, or first and second pipes. The connecting system includes: a flange of a first component set back from a free end region of the first component; a flange of a second component formed at or behind a free end region of the second component; a securing device that engages a sleeve arranged at the second component so as to axially secure and align the first and second components with respect to one another; and a jacket that at least regionally covers the first component, the second component, and the securing device.

15 Claims, 5 Drawing Sheets

Fig. 6C

Figure 1A:
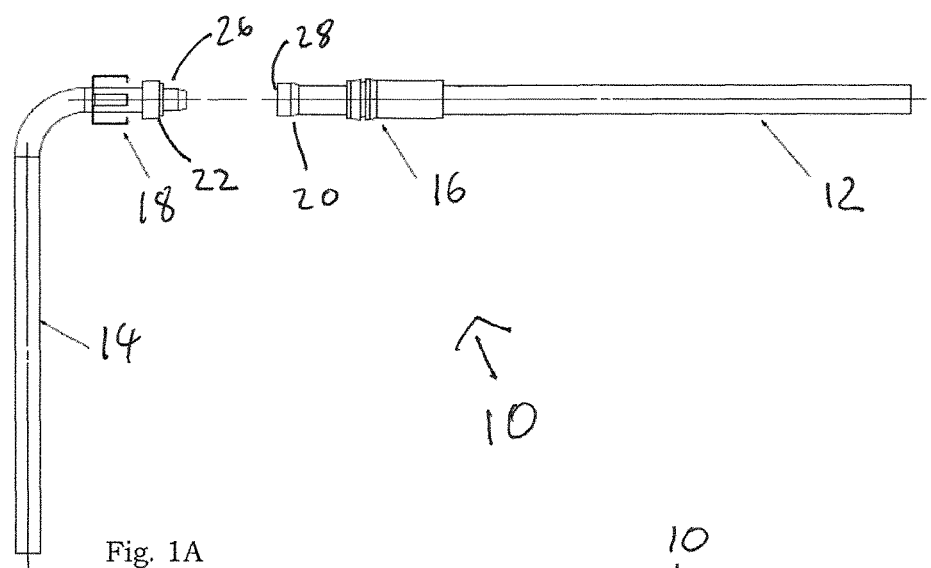

(51) Int. Cl.
*F16L 13/10* (2006.01)
*F16L 37/098* (2006.01)
*A61M 39/10* (2006.01)
*A61M 39/12* (2006.01)

(58) Field of Classification Search
USPC ............... 285/417, 242, 243, 305, 308, 309
See application file for complete search history.

(56) References Cited

U.S. PATENT DOCUMENTS

| | | | |
|---|---|---|---|
| 4,035,005 A | | 7/1977 | DeVincent et al. |
| 5,052,725 A | | 10/1991 | Meyer et al. |
| 5,104,158 A | | 4/1992 | Meyer et al. |
| 5,286,067 A | | 2/1994 | Choksi |
| 5,316,041 A | | 5/1994 | Ramacier, Jr. et al. |
| 5,374,084 A | | 12/1994 | Potokar |
| 5,447,341 A | | 9/1995 | Härtel et al. |
| 5,456,676 A | | 10/1995 | Nelson et al. |
| 5,494,074 A | | 2/1996 | Ramacier, Jr. et al. |
| 6,000,729 A | * | 12/1999 | Williamson .......... F16L 33/225 285/242 |
| 6,024,124 A | | 2/2000 | Braun et al. |
| 6,641,177 B1 | * | 11/2003 | Pinciaro ................ F16L 33/225 285/242 |
| 9,103,479 B2 | * | 8/2015 | Kertesz .................... F16L 33/28 |
| 2004/0195831 A1 | * | 10/2004 | Ohya .................... F16L 13/146 285/242 |
| 2005/0189765 A1 | * | 9/2005 | Maunder ................ F16L 33/225 285/305 |
| 2013/0103003 A1 | | 4/2013 | Capitaine et al. |
| 2016/0178101 A1 | * | 6/2016 | Blake ................. A61M 39/1011 285/417 |

FOREIGN PATENT DOCUMENTS

| | | |
|---|---|---|
| DE | 102008024360 A1 | 12/2009 |
| EP | 0499819 A1 | 8/1992 |
| EP | 0978292 A1 | 2/2000 |
| EP | 2048425 A1 | 4/2009 |
| FR | 2829219 A1 | 3/2003 |
| GB | 2217419 A | 10/1989 |
| WO | 2005022022 A1 | 3/2005 |
| WO | 2010096006 A1 | 8/2010 |

\* cited by examiner

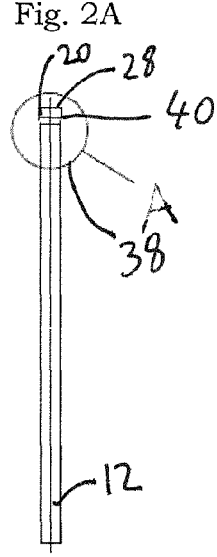
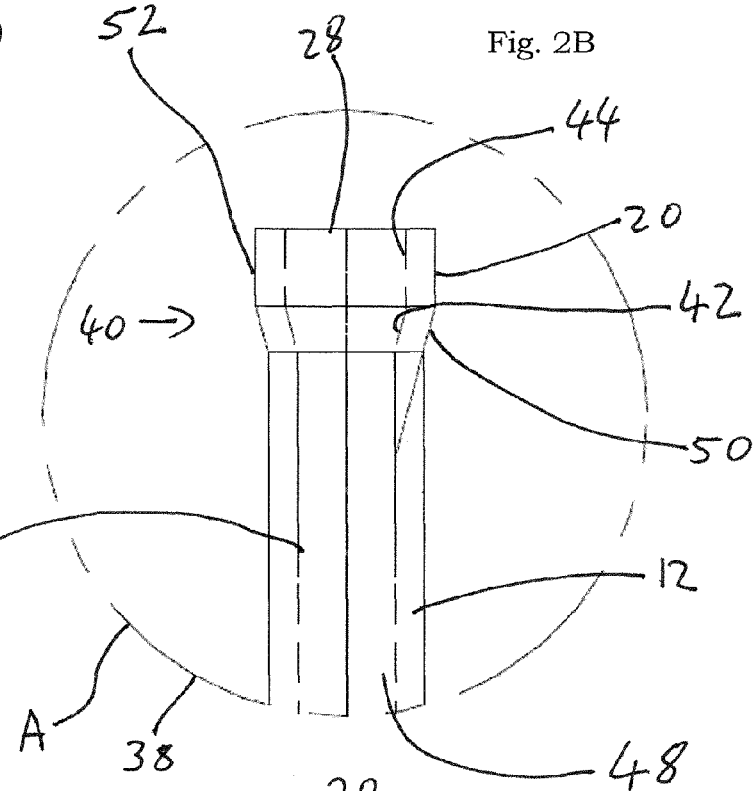
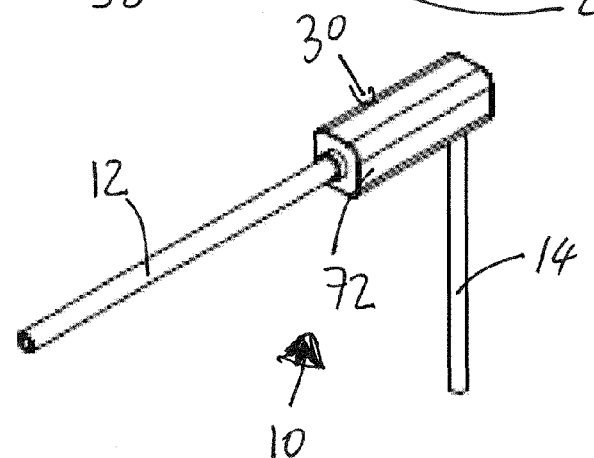
Fig. 2A
Fig. 2B
Fig. 5

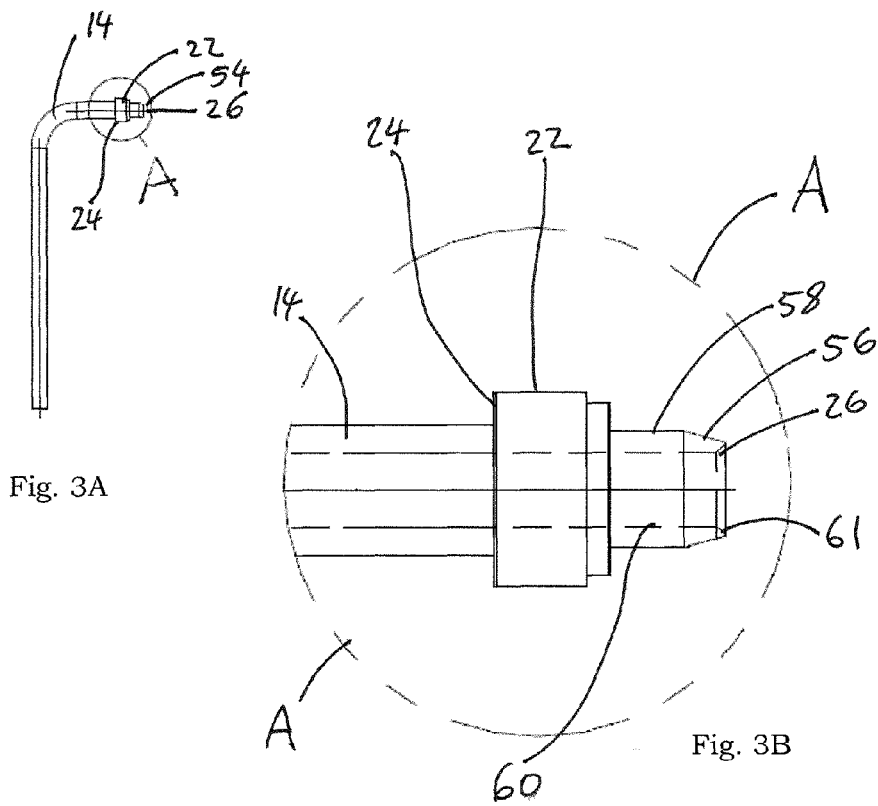
Fig. 3A
Fig. 3B
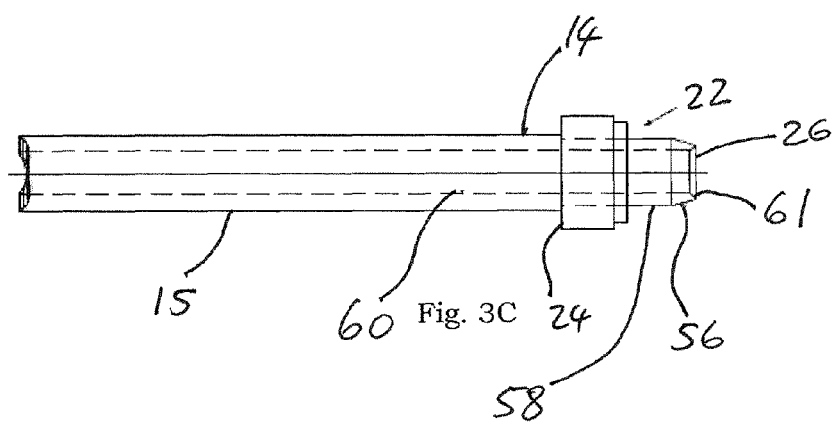
Fig. 3C

CONNECTING SYSTEM AND METHOD FOR CONNECTING FLUID-CONDUCTING COMPONENTS

The present invention relates to a connecting system for connecting two fluid conducting components, such as e.g. a first and a second hose or a hose and a connection part or a first and a second pipe, wherein the connecting system comprises a first component having a first connection region and a second component having a second connection region that cooperates with the first connection region for the formation of a connection, wherein a first flow passage is formed in the first connection region and a second flow passage is formed in the second connection region. The invention further relates to a connecting system for connecting two fluid conducting components, wherein a free end region of the one component can be plugged into a free end region of the second component, as well as to a method for the connection of two fluid conducting components.

For the analysis of liquids, e.g. by means of chromatography, fluid conducting components are connected to one another by means of a plugged connection. Such a plugged connection, for example, comprises a hose and a hollow needle, such as is described e.g. in the EP 0 978 292. On connecting the components a frequently conically formed needle end is inserted into the hose in order to push this onto the needle on an expansion of its diameter and to fix it there by means of friction. On a sliding on of the hose, on the one hand, the material of the hose is stretched, which leads to a weakening of the hose in the region of the connection and, on the other hand, also some of the hose material can be scraped off by the needle which leads to a contamination and/or an obstruction of the needle and even to a leak in the region of the connection.

Furthermore, a region of spread (also referred to as a brackish water region) is formed between the needle end and the hose on forming the plugged connection. Such regions are regions in which a liquid flow is delayed, this means that e.g. a liquid or a contamination from a previous analysis can be deposited in this region and cannot or can only be rinsed out poorly, however, can possibly mix with a liquid of a later analysis which leads to a corruption of the analysis.

A further attempt of avoiding such regions of spread consists therein of using screwable fittings. Hereby an inner thread is formed at the needle in an injection-molded process and a fitting having a corresponding outer thread loosely comprises the hose. In order that the hose cannot be pulled out of the fitting and the flow passage is sealed off between the needle and the hose, the hose end is deformed at a the right angle to the longitudinal axis of the hose and a seal is provided between the deformed hose end and the fitting. On shaping the end of the hose, a small radius results at the hose end which leads to a region of spread between the end of the needle and the deformed hose end.

Furthermore, the flow passages of the hose and the needle cannot be aligned coaxially in an exact manner which leads to further regions of spread and to a constriction of the cross-section of the flow passage in this region on the transition from the needle end to the hose end.

For this reason it is the object of the present invention to suggest a connection that leads to no or at least to no appreciable constriction of the cross-section at the transition between the flow passages of the two regions and which completely minimizes the size of the regions of spread completely or at least substantially minimizes them. Furthermore, the connection should not lead to a noticeable weakening of the material of the components and should be capable of being realized at a technologically premium quality and in a cost-effective manner.

In order to solve this object a connecting system including two components and a method of connecting the two components are provided.

In accordance with the invention the connecting system has a first component having a first connection region and has a second component having a second connection region that cooperates with the first connection region for the formation of a connection, wherein a first flow passage is formed in the first connection region and a second flow passage is formed in the second connection region. In the connected state of the connecting system the two flow passages are aligned with respect to one another and directly transition (i.e. merge) into one another with a constant cross-section or a continually tapering cross-section of at least one of the connection regions, this means they transition into one another at least substantially without a discontinuity. In the region of the connection at least one part of the first connection region and at least one part of the second connection region are connected to one another by means of a jacket, preferably in a fixing and possibly also in a sealing manner.

Due to the fact that the two flow passages are aligned with respect to one another in the connected state of the connecting system and transition into one another with a constant cross-section or with a continuously tapering cross-section of at least one of the connection regions, a connection is made available which does not bring about a cross-sectional constriction at the transition between the flow passages of the two connection regions.

The regions of spread are completely avoided or at least minimized as far as possible by means of a constant cross-section or a continuously tapering cross-section in such a way that no brackish water regions arise that lead to unwanted disturbances in the operation of the connection.

Furthermore, a connection is formed between two components, the connection being provided with a cover from the outside in order to fix the connection between the components in such a way that they are held in an aligned manner and cannot be released or at least cannot be released without further ado. Preferably, the fixing also prevents a possible loss of a seal between the two components. Moreover, the jacket can also ensure a seal and/or an additional seal of the connection. The connection regions of the respective components are manufactured in such a way that these are adapted to one another in such a way that regions of spread are not present or are minimized as far as possible and a substantially continuous internal cross-section of the two components is ensured in the region of the connection.

Preferably, the jacket forms a non-releasable connection between the first and second flanges. This means that the connection is continuous and in particular that an improved seal of the connection is produced by the jacket, as no liquid can diffuse through the jacket. When the jacket is produced in an injection-molded process a material, e.g. a liquid material, is typically introduced into an injection mold under pressure and/or at increased temperature and the material solidifies around the connection between the two components in such a way that the jacket quasi forms an integral connecting system with the two components.

The cooperating connection between the first connection region and the second connection region is preferably configured in such a way that the connection is tight, this means that no liquid or gas can emerge in the region of the connected connection regions.

In a preferred embodiment the first connection region can be plugged into the second connection region. Due to the fact that the components can be plugged together it is ensured that no clearance is present between the components which leads to the creation of regions of spread and/or to a change in cross-section. Furthermore, an additional seal is hereby created in the connection region by means of the parts, for example conically shaped parts, inserted into one another.

In accordance with a further preferred embodiment the first connection region comprises a flange set back from a free end region of the first component and the second connection region comprises a flange formed at or behind a free end region of the second component.

The use of flanges as connection regions of the components enables an even more exact connection between the two components which prevents the possibility of an occurrence of regions of spread and/or cross-sectional changes in an improved manner. Such flanges can be integrally formed at the respective component or can be retrofitted onto the respective component. Typical examples of such flanges are premanufactured extensions of hoses at hoses or pipes and holding flanges at needles or fittings. For example, a needle or a rigid component such as a pipe can be provided with an external thread onto which the flange is screwed. Having regard to a hose, the flange can be configured by an axial squashing of the hose possibly on a heating of the hose in the region of squashing. Alternatively, the end region of the hose can be crimped, for example during the formation of the internal conical shape, in order to generate a collar having an enlarged diameter which itself serves as a flange or as a connection and/or as an abutment for a flange part that can be pushed on.

In accordance with a further embodiment a securing device is provided that engages at or behind the first flange and/or at or behind the second flange in order to axially hold the first and the second component with respect to one another.

Preferably the first connection region is a flange set back from a free end region of the first component and the second connection region is a flange configured at or behind a free end region of the second component. Through the use of flanges as connection regions an improved alignment of the two flow passages can be created in the region of the transition, with the probability of constrictions of cross-sections being even further minimized in the region of the transition.

The two connection regions and/or the two flanges of the components can be fixed to one another by means of a securing device. A fixing of the components ensures an even more improved seal between the components. Furthermore, such a securing device, also following the covering, ensures that the two components cannot shift relative to one another which would lead to a non-desired accrual of regions of spread and/or to cross-sectional changes.

In a further aspect the invention comprises a connecting system for the connection of two fluid guiding components, such as a first and a second hose or a hose and a connection part or a first and a second pipe, wherein a free end region of the one component can be plugged into a free end region of the second component in such a way that a first flow passage in the first connection region and a second flow passage in the second connection region are aligned with respect to one another. Hereby the connecting system has at least the following features:
a flange at the first component that is set back from the free end region of the first component;
a flange at the second component that is configured at or behind the free end region of the second component; as well as
a securing device that engages at or behind the first flange and/or at or behind the second flange in order to axially hold the first and second component with respect to one another.

Particularly preferred embodiments of the invention are described in the subordinate claims and the drawings.

In accordance with a preferred embodiment the securing device is configured by at least one clamp by means of which the components of the connecting system can be clamped to one another. Preferably, the at least one clamp is formed at a ring part that is arranged behind the first flange or the second flange, preferably axially displaceable behind the first flange or the second flange. The at least one clamp could, however, also be configured at one of the components and could be designed in such a way that it either directly fixes the other component or fixes the other component by means of a further component. The clamp could also have the shape of a C-shaped pipe part in cross-section with inwardly projecting ring sections at its oppositely disposed ends that engage behind the flanges. Hereby the clamp could be pushed over the connection by spreading the C-shaped pipe part in a manner similar to a spring ring.

The clamp can be composed of a plastic or of a metal, wherein a clamp of metal can be produced in a stamping process from a sheet metal part. Hereby a sheet metal part having spring properties can be used and the thickness of the clamp can be reduced to a minimum.

A clamp that is possibly pre-biased can in this way simply engage at least one component after the joining of the components and fix this at the point of engagement in such a way that the components cannot shift with respect to one another. Preferably the securing device is composed of a plurality of clamps in such a way that the components are not only held and/or fixed at a single point, but at a plurality of points. For example between 1 to 20 clamps can be used in dependence on the size of the component, e.g. for Teflon hoses having an outer diameter in the region of 2.5 to 5 mm preferably between three and seven such clamps are used in order to fix the hose at the flange of the first component.

In accordance with a preferred embodiment a sleeve is arranged at the second component behind or over the second flange and the securing device and/or the at least one clamp engages at the sleeve.

By means of the sleeve a second component can be held in an even more improved manner at the first component, in particular when at least the internal shape of the sleeve is adapted to the outer shape of the second flange, as in this way the sleeve can exert a pressure on the second flange and can press this onto the flange of the first component in order to suppress a possibly previously present clearance between the components and to prevent a non-desired accrual of regions of spread and/or cross-sectional changes.

Preferably a jacket is provided that at least regionally covers the first component, the second component as well as the securing device and/or the at least one clamp. Hereby the components are additionally supported and sealed off from the outside by the means of the jacket. The jacket can be realized in a variety of ways. For example, the jacket can be realized from a plastic or an adhesive, e.g. a two-component adhesive or can be realized as a shrink tubing. The jacket can be attached independent of its formation over the complete connection including the free-lying regions of the components or only being attached over a selected region of the connection. Should further components, such as e.g. a sleeve, be additionally provided in order to improve the connection, then the jacket would also at least regionally cover the sleeve.

In accordance with a particularly preferred embodiment the jacket sealingly engages at the first and the second components and/or holds the securing device and/or the at least one clamp in a fixed manner.

The jacket thus ensures an additional seal between the components from the outside. Furthermore, the jacket brings about a strengthening of the connection of the connecting system, as the connection is provided with additional material from the outside which sealingly and also adheringly surrounds the connection and protects this. Preferably the free end regions of the jacket are configured in a tapered manner in such a way that a smooth transition results, a transition preventing a kinking of the components and/or of the hose between the jacket and the components.

In a preferred embodiment the jacket is formed by an injection-molded process. Jackets that are produced by an injection-molded process are cost-effective and can be produced in a comparatively fast and simple manner. Furthermore, the size of the connection can be adapted in a flexible manner to the size of the components of the connecting system used in that these are simply placed into an injection mold matching the size of the jacket and are covered there. Jackets that are produced by an injection-molded process are typically non-releasable and permanent.

Preferably the jacket comprises a tubular, rectangular, polygonal, oval or cylindrical outer shape. Such shapes of jackets can be easily predefined in an injection mold and also enable the covered components to be held at the jacket, e.g. by means of a further securing device as, e.g. on the use of hoses in a chromatography apparatus, the hoses have to be guided in the device, but should not be held in the region of the hoses, as a clamping of the hoses would lead to undesired cross-sectional changes.

In a further embodiment the free end region of the first component has an external conical shape and the free end region of the second component has an internal conical shape. Such conical shapes can be manufactured in a simple manner and enable a simple joining of the components on assembly of the connection of the connecting system. Furthermore, such conical shapes ensure that the components are adapted well to one another, as well as having a connection substantially free of regions of spread without noticeable cross-sectional changes between the components.

In a further preferred embodiment the connecting system has a sleeve which preferably has an internal shape that is complementary to an outer shape of the free end region of the second component and covers this at least in part. Thus, the flange of the second component can be pressed against the flange of the first component in an improved manner and ensure an improved connection between the components.

In a preferred embodiment the securing device and/or the at least one clamp engage in a groove provided at the sleeve and/or at a shoulder provided at the sleeve. The provision of such a groove and/or shoulder enables, not only a secure bond, but also a precise coordination of the length of the components with respect to one another in such a way that, as far as possible, no regions of spread arise on the connection.

In a preferred embodiment the sleeve prevents an at least substantial deformation of the free end region of the second component on forming the jacket. This is in particular true when the jacket is produced by an injection-molded process, as at least intermittently particularly high relative pressures exist during such an injection-molded process. During such an injection-molded process the sleeve also takes on a protective function in that it prevents a deformation of the flange lying there beneath and of at least a part of the connection and/or of the hose and in this way also ensures that no cross-sectional changes and/or regions of spread arise after the injection-molded process.

In accordance with a further embodiment sealing means are provided between the first and the second connection region. Such sealing means ensure a seal or an additional seal between the components with respect to the one another prior to the jacket being provided and/or for the case that no jacket is used. Such sealing means can comprise e.g. an adhesive, a silicone sealing compound or an O-ring which is introduced between the two connection regions in order to connect these to one another, preferably in a sealing manner.

A further aspect of the invention relates to a method for the connection of two fluid conducting components, the method comprising the steps of:

plugging together the components, preferably a sealing plugging together of the components;

optionally fixing the plugged together components; and connecting the plugged together components by means of a jacket produced in an injection-molded process. Such a method is typically carried out in such a way that the optionally fixed components can be placed into an injection mold that defines the shape of the jacket of the connection, before the components are covered and/or connected by means of the injection-molded process in the injection mold. By means of such a method a connecting system can be produced in a relatively simple and cost-effective manner.

Figure 1B:
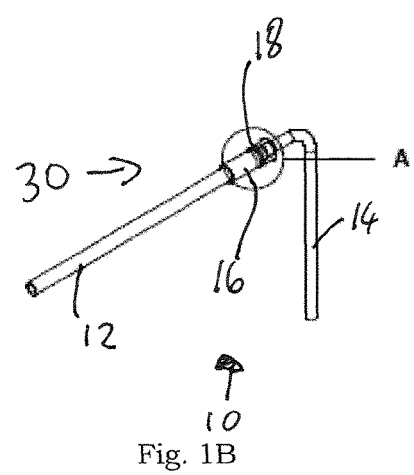
Figure 1C:
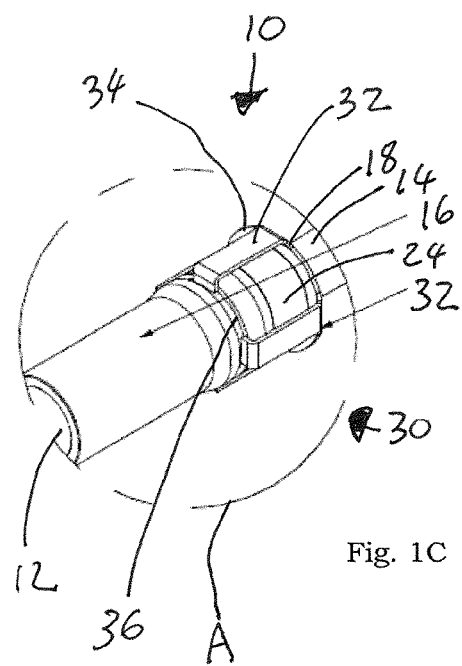
Figure 4A:
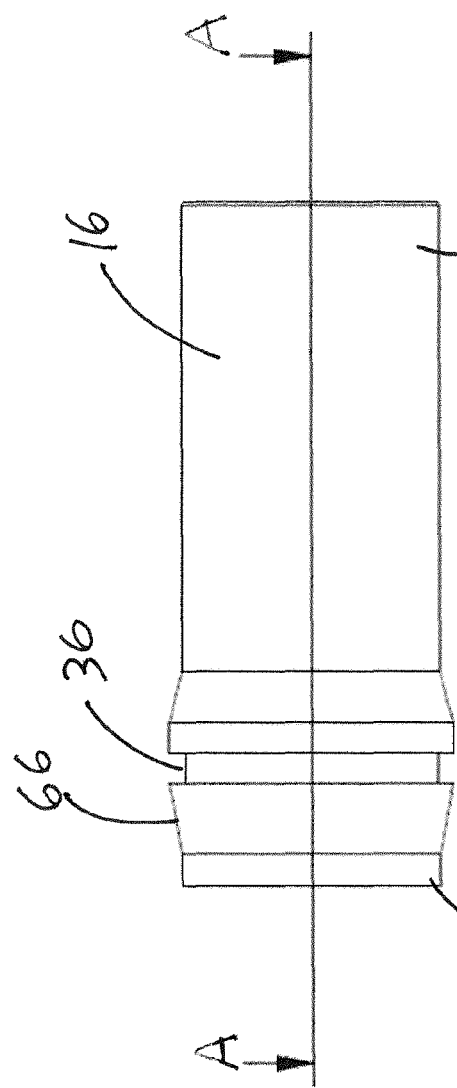
Figure 4B:
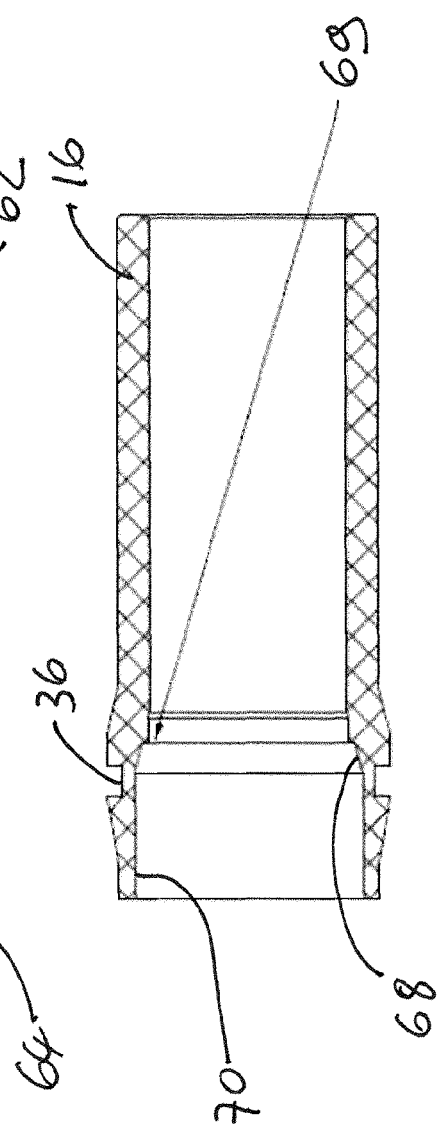
Figure 6A:
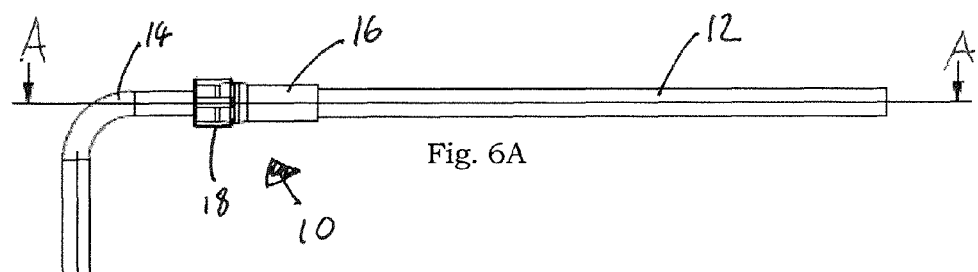
Figure 6B:
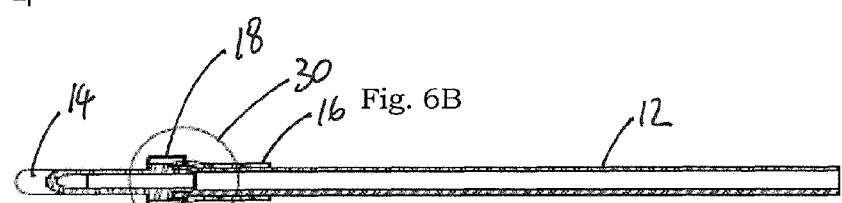
Figure 6C:
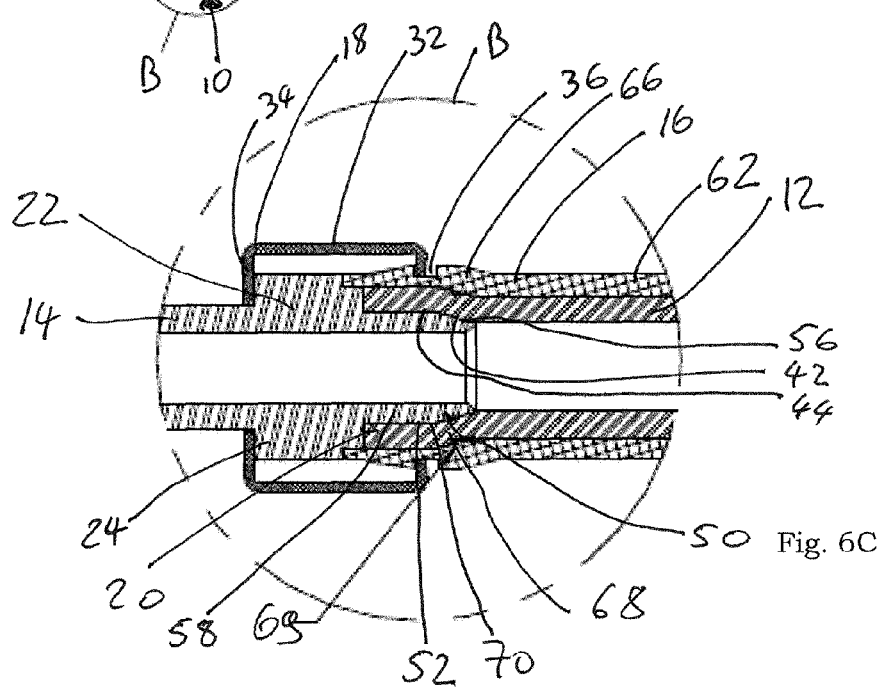

The invention will be described in detail in the following by means of embodiments with reference to the drawings in which there is shown:

FIG. 1A schematically the individual components of a connecting system in accordance with the invention prior to its assembly;

FIG. 1B the individual components of the connecting system in accordance with the invention in accordance with FIG. 1A following its assembly;

FIG. 1C a detailed view of the connecting system of FIG. 1B;

FIG. 2A a first flange of a connecting system in accordance with the invention;

FIG. 2B a detailed view of the region A of the flange in accordance with FIG. 2a;

FIG. 3A a second flange of a connecting system in accordance with the invention;

FIG. 3B a detailed view of the region A of the flange in accordance with FIG. 3A;

FIG. 3C a further detailed view of the region A of the flange in accordance with FIG. 3A;

FIG. 4A a side view of a sleeve of a connecting system in accordance with the invention;

FIG. 4B a section through the side view of the sleeve in accordance with FIG. 4A along the sectional line A-A;

FIG. 5 a schematic assembly of a further connecting system in accordance with the invention;

FIG. 6A a side view of a connecting system in accordance with the invention;

FIG. 6B an at least partially sectioned illustration of the connecting system in accordance with FIG. 6A along the sectional line A-A of the FIG. 6A; and FIG. 6C a detailed view of the region B of the FIG. 6B which shows a partially sectioned illustration of the connecting system in accordance with FIG. 6A.

With reference to the embodiment according to FIGS. 1A, 1B and 1C, the FIG. 1A schematically shows an example of a connecting system 10 prior to the assembly of the individual components 12, 14, 16, 18. The connecting system 10 comprises two fluid conducting components 12, 14, in particular a hose 12 that has a flange 20 (in the present example a so-called hose widening 20) that cooperates and/or works with a flange 22 (a so-called holding flange 22 in this example) of a connection part 14 (a so-called hollow needle in this example). Furthermore, the connecting system of the FIG. 1A comprise a sleeve 16 and a securing device 18.

On assembly of the components 12, 14, 16, 18 of the FIG. 1A to the connecting system 10 of the FIG. 1B the flange 20 respectively the hose widening of the hose 12 is guided onto the holding flange 22 of the hollow needle 14 up until the flange 20 of the hose 12 contacts an abutment 24. In this way a free end region 26 of the one component 14 is plugged into a free end region 28 of the second component 12.

In the present invention a flange is to be understood as a premanufactured connection region by means of which a further component can be connected to the premanufactured connection region, e.g. via a further flange. This means that a premanufactured connection region of a hose 12 can be a flange 20 of a component 12 e.g. in the shape of a hose widening, whereas a hollow needle 14, that can be plugged into this hose widening, can likewise have a flange 22. In other words the two connection regions of the components 12, 14 are configured in such a way that they cooperate with one another in order to achieve a connection between the two components.

The flange 20 of the hose 12 is configured at or behind the free end region 28 of the second component 12 and the flange 22 of the needle 14 is set back from the free end region 26 of the first component 14 in such a way that these can be plugged together. In order to fix the connection 30 in accordance with FIG. 1B, a sleeve 16 is guided over the outer region of the flange 20 of the hose 12 and is held by means of a securing device 18 which is arranged at and/or behind the flange 22 of the needle 14. In this way the hose 12 is held in the axial direction at the needle 14.

As can be seen from the detailed view of the FIG. 1C the securing device 18 is formed by a clamp that is provided with claws 32 that extend from a ring part 34 in the direction of the second flange 20. In particular four claws 32 are used in this example, of which two are however covered by the sleeve 16 in the drawing. The ring part 34 in the present example is axially displaceably arranged behind the flange 22 of the component 14.

The ring part 34 could, however, be integrally formed at the flange 22 in such a way that the ring part 34 is not movable relative to the flange 22 (not shown). Alternatively, a clamp, possibly having a plurality of claws (a securing device) could also be attached at the sleeve 16 that engages behind the flange 22 of the needle 22 (also not shown) in order to fix the sleeve 16 to the flange in such a way that also in this example the hose 12 is connected to the needle 14, in particular in a fixing and sealing manner.

This construction serves the purpose of fixing the second component 12—e.g. a hose or a pipe—respectively the flange 20 of the hose 12 to the flange 22 of the hollow needle 14. For this purpose the sleeve 16 is provided that is axially displaceably arranged from behind and over the flange 20 and is fastened by the claws 32 of the securing device 18 or is engaged from behind by these. The claws 32 of the securing device 18 for this purpose engage a groove 36 provided at the sleeve 16. A shoulder could, for example, also be provided at the sleeve 16 instead of a groove 36 (not shown) behind which the claws 32 snap in and which hold the sleeve 16 over the second flange 20 in the engaged state.

If a pipe should be used instead of a hose 12, then the groove 36 respectively the shoulder could also be directly provided at the outside of the pipe or directly at a flange attached at the pipe (both not shown) in such a way that no sleeve 16 would be required in order to fix the second component 12 to the first component 14. Also the securing device 18 could be fastened to the sleeve 16 and/or to the pipe and engage behind the abutment of the flange 22 of the first component 14.

A possible design of the hose 12 of the FIGS. 1A to 1C is schematically shown in detail in the FIG. 2A. A connection region 40 is provided at an end 38 of the hose 12, the connection region having a flange 20 (hose widening) that starts at the free end face 28 of the component 12. As can be seen from the detailed view of the FIG. 2B the flange 20 has an internal shape that comprises a conically shaped region 42 and a tubular region 44 of larger diameter and that is complementary to the outer shape of the flange 22 of the first component 14 (see e.g. FIG. 6C). The conically shaped region 42 is arranged between the cylindrical region 44 of larger diameter and a tubular region 46 of smaller diameter. The diameter of the region 46 of smaller diameter corresponds substantially to the diameter of a flow passage 48 of the hose 12 and (with reference to the FIG. 6C) substantially corresponds to the diameter of a flow passage (not shown) of the hollow needle 14.

Furthermore the FIGS. 2A and 2B show that the hose end 38 adjacent to the free end face 28 of the connection region 40 also has an outer shape that deviates from a typical hose shape. In particular the flange 20 of the hose 12 also comprises an external conically shaped region 50 and an external tubular shaped region 52 of larger diameter, wherein the diameter of the external tubular shaped region 52 of larger diameter is larger than the outer hose diameter.

A possible design of the hollow needle 14 of the FIGS. 1A to 1C is schematically shown in detail in the FIG. 3A. The FIGS. 3A and 3B show a hollow needle 14 as a first component. A connection region 54 is also provided in this example at an end 26 of the needle 14, the connection region having a flange 22 that is set back from the free end region 26 of the component 14. As can be seen from the FIG. 3B, the flange 22 has an outer shape that comprises an external conically shaped region 56 and an external tubular shaped region 58. The conical angle of the external conically shaped region 56 of the component 14 of the FIG. 3B corresponds to the inclination of the internal conically shaped region 42 of the component 12 of the FIG. 2B.

The diameter of the region 58 of the needle 14 is preferably slightly larger or at least substantially the same size as the diameter of the region 44 of larger diameter of the component 12 in accordance with FIG. 2B. Due to the fact that the diameter of the region 58 of larger diameter is preferably slightly larger or at least substantially the same size as the diameter of the region 44 of larger diameter of the hose widening of the hose 12, it is ensured that the conically shaped region 42 of the hose widening is pressed towards the conically shaped region 56 of the needle, as the region of larger diameter 58 so to say splices open the region of larger diameter and brings about a force-matched connection, with the connection being sealed off. In other words the tubular region 44 of the flange 20 at the end of the hose 12 preferably has an internal diameter that is smaller than the outer diameter of the tubular region 58 of the flange 22 of the hollow needle 14 in order to press the hose onto the needle so that no regions of brackish water can arise and/or in order to at least minimize their formation.

The hollow needle 14 shown in the FIGS. 3A and 3B likewise has a flow passage 60 whose diameter substantially corresponds to the diameter of the flow passage 48 of the hose 12 of the FIG. 2B. The diameter of the flow passage 60 of the needle 14 can, however, also deviate from the diameter of the flow passage 48 (not shown), e.g. is either larger than or smaller than the diameter of the flow passage 48 of the hose 12.

On use of two flow passages 48, 60 that have a substantially like diameter, a connection 30 is in this way formed between the two components 12, 14 on a plugging of the first component 14 into the second component 12, with the connection not bringing about a cross-sectional change of the flow passage 48, 60 in the region of the connection 30 and also not having any noticeable regions of spread, as the diameter of the flow passages 48, 60 are equal and the shapes which are complementary with respect to one another of the respective conically shaped regions 42, 56 form no noticeable regions of spread when the two components are connected to one another.

A transition region 61 can be seen at the end of the flange 22 that prevents the flange 20 from becoming damaged on a connection of the components 12, 14 by the flange 22. Furthermore, this transition region 61 prevents and/or minimizes the formation of non-desired regions of brackish water in the region of the connection between the two flanges 20, 22.

The transition region 61 has the effect that the material of the hose 12 is worked on in the region of the transition region 61 on a connection of the components 12, 14 in such a way that material can flow into a free space, with the free space being present in the transition region 61. In this way it is substantially prevented that cross-sectional changes of the flow passages 48, 60 are brought about in the region of the transition region 61, this means at the transition between the components 12, 14, which changes would lead to regions of spread and/or to cross-sectional changes in the region of the transition of the flow passages 48, 60 into one another.

In the specific example of the FIG. 3B the transition region 61 has the shape of a chamfer (also referred to as a bevel). Also other shapes of transition regions 61 are plausible insofar that these enable a transition between the two components 12, 14 that is substantially free of cross-sectional changes and/or of regions of brackish water.

The FIG. 3C shows a further detailed view of the regions A of the flange in accordance with FIG. 3A. The hollow needle 14 of the FIG. 3C has a shaft 15 and likewise has the tubular shaped region 58 which has a diameter that is smaller than the outer diameter of the shaft 15 of the hollow needle 14. In principle the diameter of the tubular region 58 can be selected equal to the outer diameter of the shaft 15 of the hollow needle 14.

The diameter of the tubular region 58 and the outer diameter of the shaft 15 and in this way the size of the flange 20 are selected in practice in such a way that the size of the individual components like that of the hose 12, of the hollow needle 14 and of the sleeve 16 are adapted to the respective field of use. This means that the size of the hollow needle 16 is substantially selected in such a way that a liquid amount to be conveyed can be conveyed at the predefined pressure.

The hollow needle 14 having a flange 20 can e.g. be manufactured thereby that the flange 20 having the abutment 24 is manufactured as a separate component and is placed on the shaft of a hollow needle and is fastened there by means of adhesively bonding, pressing, welding, brazing or a similar method and/or a combination of such methods. If, like in the example of FIG. 3C, the tubular region 58 has a smaller diameter than the outer diameter of the hose 15, then this smaller diameter can e.g. be produced by shaping in a lathe or the like. Alternatively, the hollow needle can already be produced with two different outer diameters and the conically shaped region 56 in such a way that premanufactured flanges 20 are simply pushed onto the region of the smaller outer diameter 58 of the hollow needle 14 and can be connected there to the hollow needle 14 in a fluid-tight and sealing manner.

The inner shape and/or the outer shape of the complementary components 12, 14 does not have to have the shape of a cone, but can, e.g. also have a stepped or a rounded shape insofar as the shape of the internal surface of the flange 20 of the second component 12 is complementary to the shape of the outer surface of the flange 22 of the first component 14 and a step-free connection is enabled between the flanges 20, 22 in such a way that no regions of spread are formed on connecting and also no cross-sectional changes arise in the region of the connection 30.

In order to fix the connection 30 between the first flange 22 and the second flange 20, the flange 20 of the second component 12 is fixed to the flange 22 of the first component 14 (see FIG. 6C) e.g. by means of a sleeve 16 (see FIG. 1A and FIG. 4A) and at least one clamp 32.

FIG. 4A shows a top view onto the outer shape of such a sleeve 16. At one of its ends 62 the sleeve 16 has a substantially continuous diameter and at its other end 64 has a region 66 having an expanded diameter in which a circumferential groove 36 is provided. The sleeve 16 is axially pushed over the flange 20 of the component 12 (see FIG. 1C) and following the contact at the abutment 24 of the first component 14 is fixed there by means of a securing device 18. The securing device 18 engages into a groove 36 provided at the sleeve 16. In order to fix the flange 20 of the hose 12, the sleeve 16 at its end 64, where the groove 36 is provided, has an internal shape that is complementary to the outer shape of the flange 20 (e.g. of the hose widening of the FIG. 2B) of the second component 12. In the example of the FIGS. 4A and 4B the sleeve comprises an internal conically shaped region 68 and an internal tubular-shaped region 70 of larger diameter, wherein the diameter of the tubular-shaped region 70 of larger diameter is larger than the outer diameter of the hose. In this connection the conical angle of the conically shaped region 68 corresponds to the conical angle of the external conically shaped region 50 of the second component 12 and also the diameter of the tubular-shaped region 70 of larger diameter is adapted to the diameter of the tubular-shaped region 52 of larger diameter of the second component 12 in such a way that the sleeve 16 can ensure a fixing of the hose 12 to the needle 14.

Furthermore, the sleeve 16 comprises a nose 69 that is arranged at the end of the conically shaped region 68. The nose 69 is configured for the purpose of wedging with the hose 12 in order to complicate and to avoid the removal of the hose 12 out of the sleeve 16. The nose 69 so to say has the function of a barb that avoids an unwanted removal of the hose 12 out of the connection 30.

The internal shape of the sleeve 16 and/or the outer shape of the complementary component 12 does not have the shape of a cone, can e.g. also have a stepped or rounded shape insofar as the shape of the outer surface of the flange 20 of the second component 12 is complementary to the shape of the inner surface of the sleeve 16. Furthermore, the sleeve 16 enables a fixing of the second component 12 at the first component 14 in such a way that following a plugging together of the components 12, 14 the connection 30 can be maintained without clearance. A clearance in the connection 30 between the components 12, 14 under some circumstances could lead to unwanted regions of spread in the region of the connection 30 and possibly prevent that the components 12, 14 are sealed off with respect to one another.

The FIG. 5 shows a further embodiment of the connecting system 10. In this the connection 30 between the two connection regions 40, 54 that are plugged into one another or onto one another respectively is surrounded by means of a jacket 72. In this connection the connection 30 between the two components 12, 14 is fixed from the outside and is optionally additionally sealed off. The jacket 72 in this way in a fixing and possibly sealing manner engages at the first and the second component 12, 14.

Should the two components be additionally fixed by means of a securing device 18, e.g. composed amongst other things of claws 32 and a sleeve 16 then the jacket 72 at least regionally also encloses these components 16, 32 and in this way leads to an even more improved connection 30 between the components 12, 14.

In the example of the FIG. 5 the jacket 72 has a substantially rectangular shape. However, the shape can be selected arbitrarily insofar as it does not negatively influence the strength and/or the tightness of the connection 30. The jacket 72 can e.g. also have a polygonal, tubular, oval or cylindrical outer shape.

The components 12, 14 to be connected to one another are placed into an injection mold (not shown) for the forming of the jacket 72. Hereby the shape of the injection mold defines the outer shape of the jacket 72. Following this the material of the jacket 72 is injected into the injection mold at an increased pressure and possibly at an increased temperature (as is known to the person of ordinary skill in the art) in an injection-molded process in such a way that the components 12, 14 contained therein are surrounded by the material of the jacket 72 and the material of the jacket 72 solidifies in the mold. The thus produced jacket 72 is non-releasably connected to the components 12, 14.

When one of the components is e.g. a hose 12, then a sleeve 16 is normally used, on the one hand, in order to hold the hose 12 better at the first component 14, e.g. a hollow needle in accordance with FIG. 3A and, on the other hand, the sleeve 16 at least substantially prevents a deformation of the hose 12 in the region of the jacket 72 on the forming of this.

During an injection-molded process relatively high pressures and possibly high temperatures exist on injecting the material of the jacket 72. These can deform the hose 12 on the transition to the needle 14, this means in the region of the flange 20 and lead to cross-sectional changes, and, amongst other things, to the formation of the regions of spread. This is substantially avoided by means of the sleeve 16. However, the sleeve 16 does not prevent the hose 12 from being pressed onto the flange 22 of the first component 14, in order to bring about and/or to increase a seal in this region between the hose 12 and the hollow needle 14.

In order to design the seal in this region in an improved manner also further sealing means (not shown), such as e.g. an O-ring or an adhesive can be provided between the two flanges 20, 22 e.g. between the conically shaped regions 42, 56.

The FIGS. 6A to 6C show a further embodiment of the connecting system 10. FIG. 6A shows a side view of the connecting system 10, the FIG. 6B shows a partly sectioned illustration of the view in accordance with FIG. 6A along the sectional line A-A of the FIG. 6A. Hereby it becomes evident how the sleeve 16 surrounds the connection region 40 of the second component 12 and presses this onto the first component 14.

A detailed view of the region B is shown in the FIG. 6C. Here one can recognize that the sleeve 16 has an internal shape that is complementary to the outer shape of the flange 20 of the hose 12 and fastens this to the first component 14, the hollow needle. One further sees that no noticeable regions of spread can be recognized due to the complementary shape of the flanges 20, 22. Such undesired regions of spread could lead to a falsification of an analysis, as in this connection deposits could form here.

It is thereby achieved that the two flow passages 48, 60 are aligned with respect to one another in the connected state of the connecting system 10 and transition into one another with a constant cross-section or a continuously tapering cross-section of at least one of the connection regions. Hereby no cross-sectional constriction is generated at the transition between the flow passages 48, 60 of the two connection regions 40, 54.

The regions of spread are also completely or at least substantially minimized by a constant cross-section or a continuously tapering cross-section of the connection regions 40, 54 and/or of the flanges 20, 22 in such a way that no regions of brackish water arise that could lead to undesired disturbances in the operation of the connection 30 and/or of the connecting system 10.

The connecting system 10 can in practice experience a plurality of different designs. For example, the following connections can be realized:

a) a connection between a hose 12, for example of Teflon and a so-called hollow needle 14 composed of metal, ceramic, zirconium oxide, sapphire or plastic;

b) a connection between two hoses that are directly adjoined next to one another;

c) a connection between two hoses that are fastened to one another via a tubular connection piece;

d) a connection between two tubular-shaped parts that can be composed of metal, ceramics, zirconium oxide, sapphire and/or plastic;

e) a connection between a hose or a pipe and a tap-like connection of a device.

The hoses that can be used in the context of the present invention comprise e.g. silicone hoses, Teflon hoses, rubber hoses, or plastic hoses etc.

In all previously mentioned examples at least the first flange 22 can be integrally formed with one of the components 12, 14 to be respectively connected to one another or at a sleeve 16 that is pushed onto the component 12, 14 or screwed to the component 12, 14. Furthermore, the securing device 18 can be formed by a clamp 32 having a plurality of claws or by individual elongated claws 32 or by a C-shaped tubular clamp 32.

REFERENCE NUMERAL LIST 10 connecting system
12 component
14 component
15 shaft
16 sleeve
18 fastening device
20 flange
22 flange
24 abutment
26 end region
28 free end face 30 connection
32 claw
34 ring part
36 groove
38 end
40 connection region
42 conically shaped region
44 region
46 region
48 flow passage
50 conically shaped region
52 region
54 connection region
56 conically shaped region
58 region
60 flow passage
61 chamfer
62 end
64 end
66 region
68 conically shaped region
69 nose
70 region
72 jacket

The invention claimed is:

1. A connecting system for connecting a first component and a second component, wherein the first and second components are fluid-guiding components, wherein a free end region of the first component can be plugged into a free end region of the second component in such a way that a first flow passage in a first connection region is aligned with respect to a second flow passage in a second connection region, the connecting system comprising:
 a flange at the first component that is set back from the free end region of the first component;
 a flange at the second component that is formed at or behind the free end region of the second component;
 a securing device that engages a sleeve that is arranged at the second component at or behind the second flange in order to axially secure and align the first and second components with respect to one another; and
 a jacket that at least regionally covers the first component, the second component, and the securing device.

2. The connecting system in accordance with claim 1, wherein the securing device is formed by at least one clamp.

3. The connecting system in accordance with claim 2, wherein the at least one clamp is formed at a ring part that is arranged behind the first flange.

4. The connecting system in accordance with claim 3, wherein the at least one clamp is a claw that extends from the ring part in a direction of the second flange and engages at the sleeve.

5. The connecting system in accordance with claim 1, wherein the jacket engages the first component and the second component in a sealing manner and secures the securing device to the first and second components.

6. The connecting system in accordance with claim 1, wherein the jacket is formed in an injection-molded process.

7. The connecting system in accordance with claim 1, wherein the jacket has a tubular, rectangular, polygonal, oval, or cylindrical outer cross-sectional shape.

8. The connecting system in accordance with claim 1, wherein the jacket forms a non-releasable connection between the first and second flanges.

9. The connecting system in accordance with claim 1, wherein the free end region of the first component has an external conical shape, and the free end region of the second component has an internal conical shape complementary to the external conical shape.

10. The connecting system in accordance with claim 1, wherein the sleeve has an internal shape that is complementary to an outer shape of the free end region of the second component and surrounds it at least in part.

11. The connecting system in accordance with claim 1, wherein the securing device engages in a groove provided at the sleeve and at a shoulder provided at the sleeve.

12. The connecting system in accordance with claim 1, wherein the sleeve at least substantially prevents a deformation of the free end region of the second component on forming the jacket.

13. The connecting system in accordance with claim 1, wherein sealing means are provided between the first connection region and the second connection region.

14. The connecting system in accordance with claim 1, wherein a transition region is provided at an end of the first component.

15. The connecting system in accordance with claim 14, wherein the transition region permits a local widening of the material of the second component in a region of a transition between the first and second flow passages.

* * * * *